United States Patent [19]

Tanabe et al.

[11] 4,113,970

[45] Sep. 12, 1978

[54] PROCESS FOR PRODUCING 1,4-DIACYLOXYBUTENE-2

[75] Inventors: Masanori Tanabe, Kurashiki; Masanori Ikeda; Nobuhiro Tamura, both of Fuji, all of Japan

[73] Assignee: Asahi Kasei Kogyo Kabushiki Kaisha, Osaka, Japan

[21] Appl. No.: 786,325

[22] Filed: Apr. 11, 1977

[30] Foreign Application Priority Data

Apr. 14, 1976 [JP] Japan .................................. 51-41421
Apr. 28, 1976 [JP] Japan .................................. 51-47769

[51] Int. Cl.$^2$ ............................................. C07C 67/05
[52] U.S. Cl. .................................. 560/244; 252/438
[58] Field of Search ................... 260/497 A; 560/244

[56] References Cited

U.S. PATENT DOCUMENTS 3,671,577  6/1972  Ono .................................. 260/497 A

FOREIGN PATENT DOCUMENTS 45-19,490  7/1970  Japan ................................. 260/497 A
1,138,366  1/1969  United Kingdom ............... 260/497 A Primary Examiner—Bernard Helfin
Assistant Examiner—Michael Shippen
Attorney, Agent, or Firm—Burgess, Dinklage & Sprung

[57] ABSTRACT 1,4-Diacyloxybutene-2 is produced with a high yield by reacting 1,3-butadiene with a carboxylic acid, for example, acetic acid, and molecular oxygen in the presence of a catalyst containing metallic palladium and at least one iodine-containing substance selected from the group consisting of iodine, iodic acid, iodates, for example, alkali metal iodates and substituted and unsubstituted ammonium iodate, and iodides, for example, hydrogen iodide, alkali metal iodide and substituted and unsubstituted ammonium iodides, the ratio in gram-atom, of iodine to palladium in the above-mentioned catalyst being 0.1 to 1.5:1.

15 Claims, 1 Drawing Figure

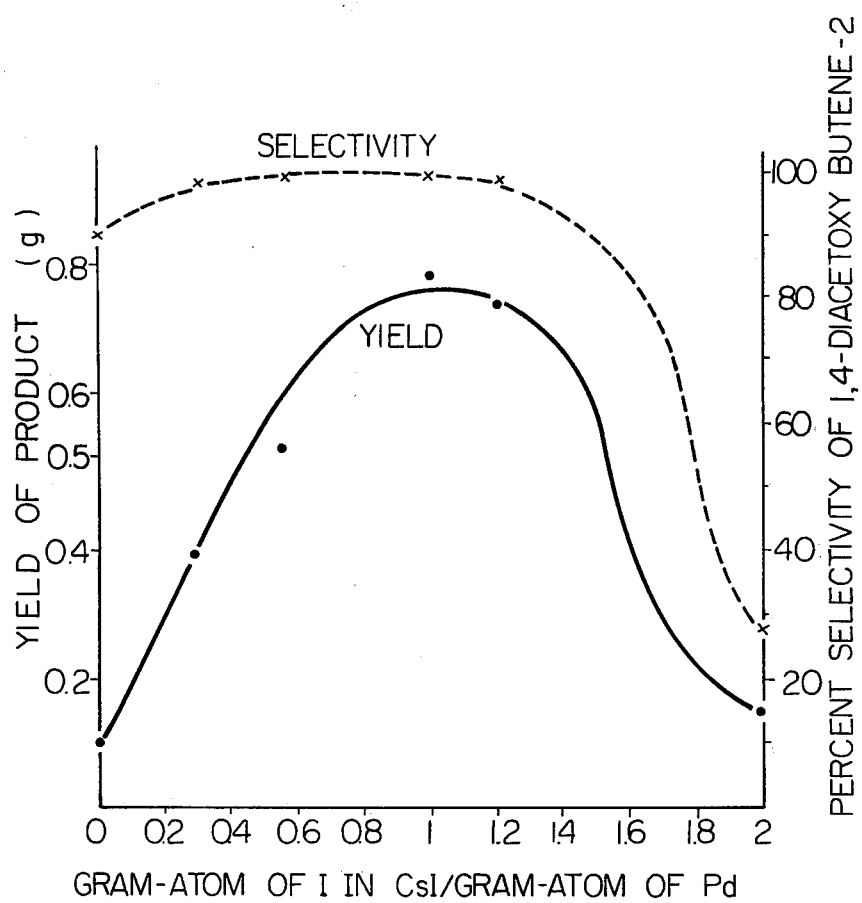

PROCESS FOR PRODUCING 1,4-DIACYLOXYBUTENE-2

The present invention relates to a process for producing 1,4-diacyloxybutene-2. More particularly, the present invention relates to a process for catalytically producing 1,4-diacyloxybutene-2 by reacting 1,3-butadiene with a carboxylic acid and molecular oxygen.

1,4-diacyloxybutene-2 is an important material, because this compound can be converted into a 1,4-butanediol useful in various chemical products by hydrogenation and hydrolysis.

In the past, various processes for producing 1,4-diacyloxybutene-2 from 1,3-butadiene were proposed. However, these processes had a disadvantage in that the products from the processes contained, as a by-product, a relatively large amount of 3,4-diacyloxybutene-1, which is useless in industry. Accordingly, these processes were not practical for employment industrially.

For example, according to Example 1 of Japanese Patent Application Laying-open No. 72090/1973, and Example 1 of Japanese Patent Application Laying-open No. 140406/1975, the proportions by weight of 1,4-diacetoxybutene-2 to 3,4-diaceloxybutene 1 in the products are 86:14 and 81:19. In order to improve the yield of 1,4-diacyloxybutene-2 in the above-mentioned processes, it is necessary to isomerize 3,4-diacyloxybutene-1 to 1,4-diacyloxybutene-2. For example, Japanese Patent Applications Laying-open Nos. 30616/1972 and 126611/1975 disclose the process for the above-mentioned isomerization. However, the necessity for the isomerization results in an increase in the number of steps in the process and, therefore, has an economical disadvantage. Further, the isomerization of 3,4-diacyloxybutene-1 has a relatively low efficiency, because 3,4-diacyloxybutene-1 is a type of vinyl compound and, therefore, has a tendency to undergo undesirable reactions.

An object of the present invention is to provide a process for producing 1,4-diacyloxybutene-2 with a high yield.

The above object is accomplished by the process of the present invention which comprises reacting 1,3-butadiene with a carboxylic acid and molecular oxygen in the presense of a catalyst which contains metallic palladium and at least one iodine-containing substance selected from the group consisting of iodine, iodic acid, iodates and iodides, the ratio in gram-atom, of iodine to palladium in the above-mentioned catalyst being 0.1 to 1.5:1.

By utilizing the process of the present invention, 1,4-diacyloxybutene-2 can be produced in a very high yield and the byproducts, that is, 3,4-diacyloxybutene-1 and 3,4-hydroxyacyloxybutene-1, are produced in a very small amount.

The catalyst usable for the process of the present invention contains metallic palladium and at least one iodine-containing substance. The iodine-containing substance is selected from the group consisting of iodine, iodic acid, iodates and iodides.

The above-mentioned iodate may be selected from the group consisting of alkali metal iodates, the iodates of the formula (I):

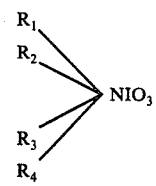

wherein $R_1$, $R_2$, $R_3$ and $R_4$ respectively denote, independently from each other, a hydrogen atom, an alkyl group preferably having 1 to 20 carbon atoms, an aralkyl group, or an aryl group, or $R_1$, $R_2$, $R_3$ and nitrogen atom altogether form a nitrogen-containing heterocyclic ring. The alkali metal iodate may be an iodate of lithium, sodium, potassium, rubidium or cesium. The iodates of the formula (I) may be ammonium iodate; a salt of iodic acid with an amine or a nitrogen-containing heterocyclic compound, for example, methylammonium iodate, dimethylammonium iodate, trimethylammonium iodate, ethylammonium iodate, n-butylammonium iodate, anilinium iodate or pyridinium iodate; and a quarternary ammonium iodate, for example, tetramethylammonium iodate, tetraethylammonium iodate, tetrabutylammonium iodate, trimethylbenzylammonium iodate, trimethyllaurylammonium iodate or trimethylphenylammonium iodate.

The iodide usable for the process of the present invention may be selected from the group consisting of hydrogen iodide, alkali metal iodides and iodides of the formula (II):

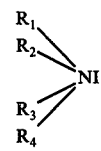

wherein $R_1$, $R_2$, $R_3$ and $R_4$ respectively denote, independently from each other, a hydrogen atom, an alkyl group preferably having 1 to 20 carbon atoms, an aralkyl group or an aryl group, or $R_1$, $R_2$, $R_3$ and nitrogen atom altogether form a nitrogen-containing heterocyclic ring.

The above-mentioned alkali metal iodide may be an iodide of lithium, sodium, potassium, rubidium or cesium. The iodides of formula (II) may be ammonium iodide; a salt of hydrogen iodide with an amine or a nitrogen-containing heterocyclic compound, for example, methylammonium iodide, dimethylammonium iodide, trimethylammonium iodide, ethylammonium iodide, n-butylammonium iodide, anilinium iodide or pyridinium iodide; or a quarternary ammonium iodide, for example, tetramethylammonium iodide, tetraethylammonium iodide, tetrabutylammonium iodide, trimethylbenzylammonium iodide, trimethylphenylammonium iodide or trimethyllaurylammonium iodide.

It is a characteristic feature of the catalyst usable for the present invention that the iodine-containing substance is used in a very small proportion by gram-atom to the metallic palladium. That is, the ratio in gram-atom of iodine to palladium in the catalyst is in a range of 0.1 to 1.5:1, preferably, 0.3 to 1.25:1.

In connection with the above-mentioned effect of the iodine-containing substance, it should be noted that substances containing a halogen other than iodine, for example, chlorine-containing substances and bromine-containing substances, have a very poor effect in producing 1,4-diacyloxybutene-2. Further, it should be noted that the remarkable increase in the percent selectivity of 1,4-diacyloxybutene-1 due to the excellent effect of iodine has never been known before the present invention. Accordingly, it is evident that the excellent effect of the catalyst of the present invention cannot be anticipated from the knowledge concerning the palladium catalyst.

The reason for how the excellent effect of the catalyst of the present invention is derived has not yet become clear. However, it is important that only when the proportion of the amount of the metallic palladium to that of the iodine in the iodine-containing substance is in a very limited range as mentioned hereinbefore, can the catalyst exhibit the above-mentioned excellent activity. This fact seems to suggest the formation of an unknown compound, for example, a complex, by the reaction of the metallic palladium with the iodine or with an iodine-containing substance, such compound exhibiting the excellent catalytic activity.

In the catalyst usable for the process of the present invention, the iodine-containing substance and the metallic palladium may be supported on a carrier. The carrier may be selected from materials usable as a carrier for known catalysts, for example, silica gel, silica-alumina, alumina, and activated carbon. The activated carbon is most preferable as the carrier of the catalyst for the process of the present invention.

The catalyst with the carrier can be prepared by the following method. A catalyst component consisting of metallic palladium supported on a carrier, for example, activated carbon, is suspended in a solution of the iodine-containing substance. The suspension is evaporated into dryness and the catalyst is obtained. The catalyst component mentioned above may be obtained from the commercial market or prepared by the following method. A carrier, for example, activated carbon is suspended in a solution of a palladium compound, for example, palladium chloride, palladium nitrate, palladium acetate, etc. The suspension is evaporated into dryness. Thereafter, the palladium compound on the carrier is converted into metallic palladium. For instance, a palladium chloride is dissolved in a solution of hydrochloric acid at a temperature of 40°-60° C. An activated carbon is suspended in the above-prepared solution and the suspension is evaporated into dryness. The resultant precursor component is brought into contact with hydrogen gas at a temperature of 200° to 600° C., to reduce the palladium chloride into metallic palladium.

It is preferable that the amount of the metallic palladium supported on the carrier is in a range from 0.5 to 20% by weight, more preferably, 1 to 8% based on the sum of the weight of the metallic palladium and that of the carrier.

There is no limitation on the type of carboxylic acid usable for the process of the present invention. However, it is preferable that the carboxylic acid be selected from the aliphatic acid having 2 to 5 carbon atoms. The most preferable carboxylic acid for the process of the present invention is acetic acid.

The molecular oxygen-containing gas to be brought into contact with the 1,3-butadiene and carboxylic acid has no limitation in the concentration of the molecular oxygen. That is, the molecular oxygen-containing gas may be a pure oxygen gas, air or a mixture of oxygen with an inert gas, for example, nitrogen and carbon dioxide.

The reaction of the 1,3-butadiene with the molecular oxygen and the carboxylic acid may be effected in a gas phase or liquid phase. However, the liquid phase reaction is preferable because of easy control of the reaction conditions. The reaction in the gas or liquid phase is preferably carried out at a temperature of 50° to 250° C., more preferably, 60° to 150° C.

In the liquid phase reaction, the 1,3-butadiene and a molecular oxygen-containing gas are introduced into a carboxylic acid-containing liquid. This liquid may consist of the carboxylic acid only or a solution of the carboxylic acid. The solution may contain a diluent which is not reactive to the 1,3-butadiene, molecular oxygen and carboxylic acid under the reaction condition of the process of the present invention. The diluent may be selected from esters such as 1,4-diacyloxybutenes-2, for example, 1,4-diacetoxybutene-2; diesters of ethylene glycol, for example, ethylene glycol diacetate, and; esters of aliphatic alcohol, for example, ethyl acetate.

In the liquid phase reaction, the catalyst is suspended preferably in the amount of 0.5 to 50 g in terms of the metallic palladium per 1 liter of the carboxylic acid-containing liquid.

The liquid or gas phase reaction may be effected under an atmospheric pressure or a pressurized condition. In the case where pressurized condition is used, the pressure is preferably 150 kg/cm2G or lower.

When the process of the present invention is carried out in the gas phase, it is preferable that the space velocity of the reaction mixture flowing through the catalyst layer falls within the range of from 100 to 50,000 hr$^{-1}$.

The following specific examples are illustrative but not limitative of the practice of the invention.

EXAMPLE 1

A catalyst was prepared by the following process. 2.5 millimoles of potassium iodate were dissolved in 100 milliliters of water. Into the resultant solution, a catalyst component which consisted of 2% by weight of palladium and the balance of carbon, and which was made by Nippon Engelhard Co., was suspended in an amount of 2.5 milligram-atoms of palladium while stirring the solution. The resultant suspension was evaporated on a steam bath into dryness. Thereafter, the resultant solid catalyst was further dried at a temperature of 120° C., under vacuum, for 2 hours.

A four-neck flask, which had a capacity of 200 milliliters and was provided with a stirrer, thermometer, tube for blowing a gas into the flask and another tube for discharging the gas from the flask, was charged with all of the above-obtained catalyst and 100 milliliters of acetic acid. The charge was heated to a reaction temperature of 100° C. and, at this temperature, 1,3-butadiene and oxygen gas were introduced at a rate of 40 milliliters/minute into the charge, respectively.

One hour after the start of the reaction, the catalyst was separated from the reaction mixture by way of filtering. The resultant filtrate was subjected to a gas-chromatographic analysis. The analysis was carried out under the following conditions.

| | |
|---|---|
| Column | Glass tube (2 m) |
| Packing | Silicon DC 550 on Diasolid L (25%) made by Nihon Chromato Co. |
| Temperature of oven | 170° C |
| Injection temperature | 180° C |

-continued

| | |
|---|---|
| He (Carrier gas) | 0.7 kg/cm$^2$G |

The result is shown in Table 1.

EXAMPLES 2 THROUGH 5

Procedures identical to those in Example 1 were carried out, except that the potassium iodate was used in amounts of 0.75 millimoles in Example 2, 1.25 millimoles in Example 3, 2 millimoles in Example 4 and 3 millimoles in Example 5. The results are shown in Table 1.

EXAMPLES 6 AND 7

The same procedures as in Example 1 were carried out, except that the reactions were effected at a temperature of 75° C. in Example 6 and 110° C. in Example 7. The results are shown in Table 1.

EXAMPLE 8

The same procedures as in Example 1 were repeated using 2.5 millimoles of iodic acid instead of the potassium iodate. The result is shown in Table 1.

EXAMPLES 9 THROUGH 12

The same procedures as in Example 1 were repeated four times by using, in place of 2.5 millimoles of potassium iodate, 0.25 millimoles of lithium iodate in Example 9, rubidium iodate in Example 10, ammonium iodate in Example 11 and tetraethylammonium iodate in Example 12. The results are shown in Table 1.

EXAMPLE 13

A catalyst was prepared by the following process. 2.5 millimoles of palladium chloride were dissolved in a solution of 0.5 milliliters of concentrated hydrochloric acid in 100 milliliters of water by heating the mixture on a hot-water bath at a temperature of 40° to 60° C. 13.0 grams of activated carbon having a 30 to 50 mesh size, which had been produced from coconut shell, was suspended in the above-prepared solution. The suspension was left to stand for 2 hours without agitation and, thereafter, evaporated to dryness. The resultant solid consisting of the activated carbon adsorbing the palladium chloride was charged into a glass reaction tube and the charge was dried by flowing nitrogen gas through the tube at a rate of 200 ml/min, at a temperature of 150° C., for 2 hours. Thereafter, the charge was heated to a temperature of 300° C. and, at this temperature, hydrogen gas was flowed through the charge at a rate of 200 ml/min, for 3 hours, to reduce the palladium chloride to metallic palladium. The product was washed with water and dried under vacuum at a temperature of 120° C. All of the dryed product consisting of metallic palladium carried on the carbon was suspended in a solution of 2.5 ml of tetrabutyl ammonium iodate in 100 ml of water while stirring the solution. The suspension was evaporated on a steam bath into dryness and further dried at a temperature of 120° C., under vacuum, for 2 hours.

The same reaction as in Example 1 was effected using the above-prepared catalyst. The result is shown in Table 1.

COMPARISON EXAMPLE 1

Procedures identical to those in Example 1 were carried out using 5 millimoles of potassium iodate. The result is shown in Table 1.

COMPARISON EXAMPLES 2 THROUGH 4

Procedures identical to those in Example 1 were repeated using, in place of 2.5 millimoles of potassium iodate, 2.5 millimoles of potassium chlorate in Comparison Example 2, potassium bromate in Comparison Example 3 and bromic acid in Comparison Example 4. The results are shown in Table 1.

COMPARISON EXAMPLE 5

The same procedures as in Example 1 were carried out, except that no potassium iodate was used, and the catalyst component consisting of metallic palladium carried on carbon was directly mixed with 100 ml of acetic acid in the four-neck flask. The result is shown in Table 1.

Table 1

| Example No. | Halogen-containing substance | Ratio in gram-atom, of halogen to palladium | Reaction temperature (° C) | Amount of resultant product (g) (*1) | Percent selectivity of 1,4-diacetoxybutene-2 (*2) |
|---|---|---|---|---|---|
| 1 | KIO$_3$ | 1 | 100 | 1.33 | 99 |
| 2 | " | 0.3 | " | 0.77 | 98 |
| 3 | " | 0.5 | " | 1.03 | 99 |
| 4 | " | 0.8 | " | 1.15 | 99 |
| 5 | " | 1.2 | " | 1.01 | 97 |
| 6 | " | 1 | 75 | 0.96 | 99 |
| 7 | " | 1 | 110 | 1.43 | 98 |
| 8 | HIO$_3$ | 1 | 100 | 1.30 | 99 |
| 9 | LiIO$_3$ | 1 | " | 1.27 | 99 |
| 10 | RbIO$_3$ | 1 | " | 1.13 | 99 |
| 11 | NH$_4$IO$_3$ | 1 | " | 1.29 | 99 |
| 12 | Et$_4$NIO$_3$ | 1 | " | 1.35 | 99 |
| 13 | Bu$_4$NIO$_3$ | 1 | " | 1.40 | 99 |
| Comparison Example 1 | KIO$_3$ | 2 | " | 0.68 | 20 |
| Example 2 | KClO$_3$ | 1 | " | Very small | — |
| Example 3 | KBrO$_3$ | 1 | " | " | — |
| Example 4 | HBrO$_3$ | 1 | " | " | — |
| Example 5 | None | 0 | " | 0.39 | 89 |

(*1) An amount of a resultant mixture of 1,4-diacetoxybutene-2, 3,4-diacetoxybutene-1 and 3,4-hydroxyacetoxybutene-1.
(*2) Ratio by weight of 1,4-diacetoxybutene-2 to the resultant mixture.

EXAMPLE 14

A four-neck flask, having a capacity of 200 ml and provided with a stirrer, thermometer, tube for blowing a gas into the flask and tube for discharging the gas from the flask, was charged with 100 ml of acetic acid. Thereafter, 2.5 millimoles of tetrabutylammonium iodide was dissolved in the acetic acid. A catalyst component consisting of activated carbon carrying thereon 5% by weight of metallic palladium, and made by Nippon Engelhard Co., was suspended in the above-obtained solution while stirring the solution. The catalyst contained 2.5 milligram-atoms of metallic palladium. The resultant suspension was stirred for 2 hours. After the suspension was heated to a temperature of 100° C., 1,3-butadiene and oxygen gas were introduced into the suspension at a rate of 40 ml/min, respectively, for 1 hour. Then, the catalyst was separated from the reaction mixture by filtering and the filtrate was subjected to a gas chromatographic analysis. The result is shown in Table 2.

EXAMPLES 15 THROUGH 17

Procedures identical to those in Example 14 were effected using, in place of tetrabutylammonium iodide, tetraethylammonium iodide in Example 15, triethylbenzylammonium iodide in Example 16 and trimethylphenylammonium iodide in Example 17. The results are shown in Table 2.

EXAMPLE 18

2.5 millimoles of ammonium iodide was dissolved in 100 ml of water. A catalyst component consisting of activated carbon carrying thereon 5% by weight of metallic palladium, and made by Nippon Engelhard Co., was suspended in the above-obtained solution while stirring. The catalyst contained 2.5 milligram-atoms of metallic palladium. The suspension was allowed to stand for 2 hours without stirring. Thereafter, the suspension was evaporated on a steam bath into dryness, and the resultant solid was dried at a temperature of 120° C., under vacuum, for 3 hours.

All of the resultant catalyst and 100 ml of acetic acid was charged into a four-neck flask having a capacity of 200 ml, and provided with a stirrer, thermometer, tube for blowing a gas into the flask and tube for discharging the gas from the flask, and heated to a temperature of 100° C. The resultant mixture was subjected to the same operations as in Example 14. The result is shown in Table 2.

EXAMPLE 19

The same operations as in Example 18 were repeated using 2.5 millimoles of pyridinium iodide in place of the ammonium iodide. The result is shown in Table 2.

EXAMPLE 20

The same procedures as those in Example 14 were effected except that a catalyst made by the same method as that in Example 13 was used in place of the catalyst of Example 14. The result is shown in Table 2.

COMPARISON EXAMPLE 6

The same procedures as in Example 14 were carried out, except that tetrabutylammonium iodide was used in an amount of 5 millimoles. The result is shown in Table 2.

COMPARISON EXAMPLES 7 AND 8

The same procedures as in Example 14 were carried out using, instead of tetrabutylammonium iodide, tetraethylammonium chloride in Comparison Example 7 and tetraethylammonium bromide in Comparison Example 8. The results are shown in Table 2.

Table 2

| Example No. | Halogen containing compound | Ratio in gram-atom, of halogen to palladium | Reaction temperature (° C) | Amount of resultant product (g) | Percent selectivity of 1,4-diacetoxy-butene-2 |
|---|---|---|---|---|---|
| 14 | $Bu_4NI$ | 1 | 100 | 1.01 | 99 |
| 15 | $Et_4NI$ | 1 | " | 0.65 | 99 |
| 16 | $Et_3 C_6H_5CH_2NI$ | 1 | " | 0.68 | 99 |
| 17 | $Me_3C_6H_5NI$ | 1 | " | 0.58 | 99 |
| 18 | $H_4NI$ | 1 | " | 0.55 | 99 |
| 19 | ⟨◯⟩NHI | 1 | " | 0.65 | 99 |
| 20 | $Bu_4NI$ | 1 | " | 1.45 | 99 |
| Comparison Example 6 | $Bu_4NI$ | 2 | " | Very small | — |
| Example 7 | $Et_4NCl$ | 1 | " | 0.05 | 40 |
| Example 8 | $Et_4NBr$ | 1 | " | 0.10 | 65 |

EXAMPLE 21

A four-neck flask having a capacity of 200 ml, and provided with a stirrer, thermometer, inlet for introducing a gas into the flask and outlet for discharging the gas from the flask, was charged with 100 ml of acetic acid, 3.18 g of a catalyst component consisting of carbon carrying thereon 5% by weight of metallic palladium, and made by Nippon Engelhard Co., which component contained 1.5 milligram-atoms of the metallic palladium and 0.190 g (0.75 millimoles) of iodine. The mixture was allowed to stand for one hour at an ambient temperature. The mixture was, thereafter, heated to a temperature of 100° C. and a flow of 1,3-butadiene, at a rate of 60 ml/min, and a flow of oxygen gas, at a rate of 30 ml/min, were introduced into the mixture in the flask. Two hours after the start of the introduction of 1,3-butadiene and oxygen gas, the catalyst was separated from the reaction mixture by way of filtration. The filtrate was subjected to a gas chromatographic analysis. The result is shown in Table 3.

EXAMPLE 22

The same procedures as shown in Example 21 were effected, except that the iodine was used in an amount of 0.038 g (0.15 millimoles). The result is shown in Table 3.

COMPARISON EXAMPLE 9

The same procedures as in Example 21 were repeated using 0.120 g (0.75 millimoles) of bromine in place of 0.190 g of iodine. The result is shown in Table 3.

COMPARISON EXAMPLE 10

The same operations as in Example 21 were effected, except that no catalyst component consisting of carbon carrying thereon the metallic palladium was used. That is, the catalyst consisted of iodine only. The result is shown in Table 3.

Table

| Ex. No. | Catalyst | Ratio, expressed in gram-atom, of halogen to palladium | Amount of product (g) | Percent selectivity of 1,4-diacetoxy-butene-2- |
|---|---|---|---|---|
| 21 | Pd - $I_2$ | 1 | 1.46 | 98.3 |
| 22 | Pd - $I_2$ | 0.3 | 0.94 | 98.0 |
| Comparison Ex. 9 | Pd - $Br_2$ | 1 | 0.21 | 85.0 |
| Ex. 10 | $I_2$ | — | 0 | — |

EXAMPLE 23

5.3 g of a catalyst component, consisting of activated carbon carrying thereon 5% by weight of metallic palladium and made by Nippon Engelhard Co., which component contained 2.5 milligram-atoms of metallic palladium, were suspended in a solution of 2.5 millimoles of cesium iodide in 70 ml of water while stirring the solution. The suspension was evaporated to dryness on a steam bath and, then, the resultant solid was dried at a temperature of 120° C. under vacuum.

All of the above-obtained catalyst and 100 ml of acetic acid was charged into a four-neck flask having a volume of 200 ml, and provided with a stirrer, thermometer, inlet tube for gas and outlet tube for the gas. The charge was heated to a temperature of 110° C. and, then, 1,3-butadiene and oxygen gas were blown into the charge at a flow rate of 60 ml/min, for 1 hour, respectively. Then, the reaction mixture was filtered to separate the catalyst therefrom. The filtrate was subjected to a gas chromatographic analysis. The result is shown in Table 4.

Additionally, it was determined that the content of iodine in the filtrate was less than 1.5 ppm, which is a lower limit of the content of iodine which can be detected. From this fact, it is obvious that 99.5% or more of iodine, based on the entire amount of the iodine used, were maintained on the catalyst and less than 0.5% of iodine, based on the entire amount of the iodine used, were dissolved in the filtrate.

EXAMPLES 24 THROUGH 26

Procedures identical to those in Example 23 were carried out except that cesium iodide was used in amounts of 1.25 millimoles in Example 24, 3.0 millimoles in Example 25 and 0.75 millimoles in Example 26. The results are indicated in Table 4.

EXAMPLES 27 THROUGH 30

The same procedures as in Example 23 were effected using, in place of cesium iodide, rubidium iodide in Example 27, potassium iodide in Example 28, sodium iodide in Example 29 and hydrogen iodide in Example 30, respectively, in an amount of 2.5 millimoles.

COMPARISON EXAMPLE 11

The same procedures as in Example 23 were carried out except that the cesium iodide was used in an amount of 5 millimoles. The result is shown in Table 4.

COMPARISON EXAMPLES 12 THROUGH 14

The same procedures as in Example 23 were effected using 2.5 millimoles of cesium chloride in Comparison Example 12, cesium bromide in Comparison Example 13 and potassium chloride in Comparison Example 14, in place of the cesium iodide. The results are indicated in Table 4.

COMPARISON EXAMPLE 15

The same procedures as in Example 23 were effected, except that no cesium iodide was used. The result is shown in Table 4.

Table 4

| Example No. | Halogen-containing compound | Ratio in gram-atom, of halogen to palladium | Amount of product (g) | Composition of product (%) | | |
|---|---|---|---|---|---|---|
| | | | | 1,4-di-acetoxy-butene-2 | 3,4-di-acetoxy-butene-1 | 3,4-hydro-xyacetoxy-butene-1 |
| 23 | CsI | 1 | 0.78 | 99 | 1 | — |
| 24 | " | 0.5 | 0.51 | 99 | 1 | — |
| 25 | " | 1.2 | 0.74 | 98 | 2 | — |
| 26 | " | 0.3 | 0.38 | 97 | 3 | — |
| 27 | RbI | 1 | 0.92 | 99 | 1 | — |
| 28 | KI | 1 | 0.55 | 99 | 1 | — |
| 29 | NaI | 1 | 0.54 | 99 | 1 | — |
| 30 | HI | 1 | 0.49 | 98 | 2 | — |
| Comparison Example 11 | CsI | 2 | 0.15 | 27 | — | 73 |
| Example 12 | CsCl | 1 | 0.23 | 48 | 38 | 14 |
| Example 13 | CsBr | 1 | 0.15 | 59 | — | 41 |
| Example 14 | KCl | 1 | Very small | — | — | — |
| Example 15 | None | — | 0.15 | 90 | 10 | — |

The drawing is a graph showing the relationships of the ratio of the amount of cesium iodide in millimole to that of palladium in milligram-atom, in the catalyst, to the amount in grams of the product and the percent selectivity of 1,4-diacetoxybutene-2. The graph was prepared from the results of Examples 23 through 26 and Comparison Examples 11 and 15. From the graph, it is evident that the mixing ratio of the iodine-containing substance to the palladium in the catalyst is very important for obtaining the desired product in a high yield. Even if the cesium iodide is replaced by iodine, iodic acid, iodate, hydrogen iodide, ammonium iodide and an iodide of a metal other than cesium, a similar relationship to that mentioned above was obtained.

EXAMPLES 31 AND 32

A catalyst was prepared by the same method as in Example 27. 10 ml of the catalyst were charged into a reaction tube having an inside diameter of 10 mm. Acetic acid at a flow rate of 27 ml/hr, 1,3-butadiene at a flow rate of 60 ml/min, and oxygen at a flow rate of 30 ml/min were fed into the reaction tube at a temperature of 80° C. in Example 32 and 100° C. in Example 32.

The results occurring two hours after the start of the reactions are shown in Table 5.

Table 5

| Example No. | Temperature (° C) | Yield of product (g/hr) | Percent selectivity of 1,4-diacetoxybutene-2 |
|---|---|---|---|
| 31 | 80 | 0.81 | 96 |
| 32 | 100 | 0.90 | 94 |

EXAMPLE 33

The same procedures as in Example 1 were carried out, except that 100 ml of propionic acid were used in place of 100 ml of the acetic acid. One hour after the start of the reaction, it was observed that the resultant product consisted of 0.95 g of 1,4-dipropionyloxybutene-2 and a negligible amount of 3,4-dipropionyloxybutene-1.

What we claim is:

1. A process for producing 1,4-diacyloxybutene-2 comprising reacting 1,3-butadiene with an aliphatic carboxylic acid having 2 to 5 carbon atoms and molecular oxygen in the presence of a catalyst which contains metallic palladium and at least one iodine-containing substance selected from the group consisting of iodine; iodic acid; alkali metal iodates; iodates of the formula (I):

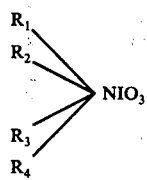

hydrogen iodide; alkali metal iodides; and iodides of the formula (II):

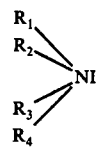

wherein $R_1$, $R_2$, $R_3$ and $R_4$ each independently is a hydrogen atom, an alkyl group having 1 to 20 carbon atoms, an aralkyl group or an aryl group, or $R_1$, $R_2$, $R_3$ and the nitrogen atom together form a nitrogen-containing heterocyclic ring, the ratio in gram-atom of iodine to metallic palladium in said catalyst being 0.1 to 1.5:1.

2. A process as claimed in claim 1, wherein said ratio in gram-atom of iodine to metallic palladium in said catalyst is 0.3 to 1.25:1.

3. A process as claimed in claim 1, wherein said metallic palladium and said iodine-containing substance are supported on a carrier.

4. A process as claimed in claim 1, wherein said aliphatic carboxylic acid is acetic acid.

5. A process as claimed in claim 1, wherein said 1,3-butadiene and said molecular oxygen respectively are brought into contact with said carboxylic acid in the liquid phase.

6. A process as calimed in claim 1, wherein said reaction is effected at a temperature of 50° to 250° C.

7. A process as claimed in claim 1, wherein said iodine-containing substance is selected from the group consisting of alkali metal iodates and iodates of the formula (I).

8. A process as claimed in claim 1, wherein said iodine-containing substance is selected from the group consisting of hydrogen iodide, alkali metal iodides and iodides of the formula (II).

9. A process as claimed in claim 3 wherein, said catalyst is prepared by mixing a catalyst component consisting of a carrier and metallic palladium with a solution of at least one said iodine-containing substance and evaporating said mixture into dryness.

10. A process as claimed in claim 9, wherein said catalyst component is prepared by suspending a carrier in a solution of a palladium compound, evaporating said suspension into dryness and converting said palladium compound on said carrier into metallic palladium.

11. A process as claimed in claim 10, wherein said palladium compound is palladium chloride, palladium nitrate or palladium acetate.

12. A process as claimed in claim 3, wherein said carrier is activated carbon.

13. A process as claimed in claim 3, wherein the content of said metallic palladium on said carrier is in a range of 0.5 to 20% by weight.

14. A process as claimed in claim 13, wherein said content of said metallic palladium on said carrier is in a range from 1 to 8% by weight.

15. A process as claimed in claim 1, wherein said metallic palladium is present in an amount of 0.5 to 50 g per liter of said carboxylic acid solution.

* * * * *